(12) United States Patent
Harigaya et al.

(10) Patent No.: US 10,408,749 B2
(45) Date of Patent: Sep. 10, 2019

(54) IMAGING METHOD, IMAGING APPARATUS, IMAGING SYSTEM, SURGERY SUPPORT SYSTEM, AND A STORAGE MEDIUM

(71) Applicants: JAPAN ORGANIZATION OF OCCUPATIONAL HEALTH AND SAFETY, Kawasaki-shi, Kanagawa (JP); NATIONAL INSTITUTE OF ADVANCED INDUSTRIAL SCIENCE AND TECHNOLOGY, Chiyoda-ku, Tokyo (JP); NIKON CORPORATION, Minato-ku, Tokyo (JP)

(72) Inventors: Kenichi Harigaya, Ichihara (JP); Daisuke Ozaki, Ichihara (JP); Yuzuru Ikehara, Tsukuba (JP); Hiroki Ishikawa, Tokyo (JP); Zhen Liu, Tokyo (JP); Takeshi Hataguchi, Tokyo (JP)

(73) Assignees: JAPAN ORGANIZATION OF OCCUPATIONAL HEALTH AND SAFETY, Kawasaki-Shi (JP); NATIONAL INSTITUTE OF ADVANCED INDUSTRIAL SCIENCE AND TECHNOLOGY, Tokyo (JP); NIKON CORPORATION, Tokyo (JP)

( * ) Notice: Subject to any disclaimer, the term of this patent is extended or adjusted under 35 U.S.C. 154(b) by 0 days.

(21) Appl. No.: 15/922,999

(22) Filed: Mar. 16, 2018

(65) Prior Publication Data
US 2018/0202924 A1   Jul. 19, 2018

Related U.S. Application Data

(63) Continuation of application No. PCT/JP2016/076861, filed on Sep. 12, 2016.

(30) Foreign Application Priority Data

Sep. 18, 2015 (JP) .................................. 2015-184973

(51) Int. Cl.
*G01N 21/3563* (2014.01)
*G01N 33/483* (2006.01)
(Continued)

(52) U.S. Cl.
CPC ....... *G01N 21/3563* (2013.01); *A61B 5/0073* (2013.01); *A61B 5/0091* (2013.01);
(Continued)

(58) Field of Classification Search
CPC . A61B 5/0091; A61B 5/0073; A61B 10/0233; G01N 21/4795; G01N 33/4833;
(Continued)

(56) References Cited

U.S. PATENT DOCUMENTS

| 5,840,035 A | 11/1998 | Heusmann et al. |
| 2004/0097810 A1 | 5/2004 | Miwa |

(Continued)

FOREIGN PATENT DOCUMENTS

| JP | 2006-102360 A | 4/2006 |
| JP | 2007-075445 A | 3/2007 |
| WO | WO-2014/192876 A1 | 12/2014 |

*Primary Examiner* — David P Porta
*Assistant Examiner* — Fani Boosalis
(74) *Attorney, Agent, or Firm* — Foley & Lardner LLP

(57) ABSTRACT

An imaging method includes: irradiating breast tissue with infrared light, detecting light in a narrow wavelength band selected from wavelength bands from 1400 nm or more to 1600 nm or less, among light radiated from the tissue irradiated with the infrared light, and generating, based on the detected light in the narrow wavelength band, an image to specify an area in the tissue containing breast cancer cell aggregation or breast cancer tissue.

34 Claims, 39 Drawing Sheets

(51) Int. Cl.
*A61B 5/00* (2006.01)
*G01N 21/47* (2006.01)
*A61B 5/117* (2016.01)
*G01N 21/359* (2014.01)
*A61B 10/02* (2006.01)

(52) U.S. Cl.
CPC ............ *A61B 5/117* (2013.01); *A61B 5/4842* (2013.01); *G01N 21/4795* (2013.01); *G01N 33/4833* (2013.01); *A61B 5/0077* (2013.01); *A61B 10/0233* (2013.01); *G01N 21/359* (2013.01); *G01N 2201/062* (2013.01); *G01N 2201/06113* (2013.01)

(58) Field of Classification Search
CPC ..... G01N 2201/06113; G01N 21/3563; G01N 21/359; G01N 33/483
See application file for complete search history.

(56) References Cited

U.S. PATENT DOCUMENTS

| | | |
|---|---|---|
| 2007/0027362 A1 | 2/2007 | Handa et al. |
| 2016/0139039 A1 | 5/2016 | Ikehara et al. |
| 2016/0290926 A1* | 10/2016 | Notingher .......... G01N 33/4833 |

* cited by examiner

IMAGING METHOD, IMAGING APPARATUS, IMAGING SYSTEM, SURGERY SUPPORT SYSTEM, AND A STORAGE MEDIUM

CROSS REFERENCE TO RELATED APPLICATION

This is a Continuation of PCT Application No. PCT/JP2016/076861, filed on 12 Sep. 2016. The contents of the above-mentioned application are incorporated herein by reference.

FIELD OF THE INVENTION

The present invention relates to an imaging method, an imaging apparatus, an imaging system, a surgery support system, and a storage medium.

BACKGROUND

Recently, there have been an increasing awareness of and a higher interest in breast cancer. To provide early detection of breast cancer, for example, clinical diagnoses using mammography, ultrasound imaging, or the like (screening inspections) have been widely performed. When a breast cancer is detected, surgical resection is performed in principle. The resected tissue is subjected to pathological diagnosis (pathological inspection) under a microscope to make sure that, for example, the tissue of breast cancer has been completely excised. Furthermore, as an example technique used to inspect body tissue, a technique of Patent Literature 1 (Japanese Application Publication No. 2006-102360) is proposed. The technique according to the Patent Literature 1 relates to, for example, an apparatus of irradiating body tissue with infrared light, acquiring an image of subcutaneous vessels on the basis of the infrared light reflected by the body tissue, and displaying biometric information.

Because inspections and diagnoses of breast cancer require accuracy, it is desired that reliable information on a breast cancer area, such as breast cancer tissue, be acquired. However, human body tissues have optical properties such as light absorbance, transmittance, and reflectance that vary depending on the composition of the human body, and this difference may make it difficult to obtain reliable information on breast cancer areas.

SUMMARY

A first aspect of the present invention provides an imaging method including: irradiating breast tissue with infrared light, detecting light in a narrow wavelength band selected from wavelength bands from 1400 nm or more to 1650 nm or less, among light radiated from the tissue irradiated with the infrared light, and generating, based on the detected light in the narrow wavelength band, an image to specify an area in the tissue containing breast cancer cell aggregation or breast cancer tissue.

A second aspect of the present inspection provides an imaging apparatus including: an irradiator that irradiates breast tissue with infrared light, a detector that detects light in a narrow wavelength band selected from wavelength bands from 1400 nm or more to 1650 nm less, among light radiated from the tissue irradiated with the infrared light, and an image generator that generates, based on detection results from the detector, an image to specify an area in the tissue containing breast cancer cell aggregation or breast cancer tissue.

A third aspect of the present invention provides an imaging apparatus including: an irradiator that irradiates tissue with light, a detector that detects first light in a wavelength band selected from predetermined wavelength bands from 1050 nm or more to 1650 nm or less, among light radiated from the tissue irradiated with the light, and an image generator that generates, based on detection results from the detector, an image to specify a breast cancer area in the tissue.

A fourth aspect of the present invention provides an imaging system including: the imaging apparatus in the second aspect or the third aspect and a display device that displays images of the tissue captured by the imaging apparatus.

A fifth aspect of the present invention provides a surgery support system including: the imaging apparatus in the second aspect and an operation device that is capable of processing tissue.

A sixth aspect of the present invention provides a storage medium storing therein a control program that causes a computer to control processing including: irradiating breast tissue with infrared light, detecting light in a narrow wavelength band selected from wavelength bands from 1400 nm or more to 1650 nm or less, among light radiated from the tissue irradiated with the infrared light, and generating, based on the detected light in the narrow wavelength band, an image to specify an area in the tissue containing breast cancer cell aggregation or breast cancer tissue.

A seventh aspect of the present invention provides a storage medium storing therein a control program that causes a computer to control processing including: irradiating tissue with light, detecting first light in a wavelength band selected from predetermined wavelength bands from 1050 nm or more to 1650 nm or less, among light radiated from the tissue irradiated with the light, and generating, based on the detected first light, an image to specify an area in the tissue containing breast cancer.

DETAILED DESCRIPTION OF EMBODIMENTS

First Embodiment

Figure 1A:
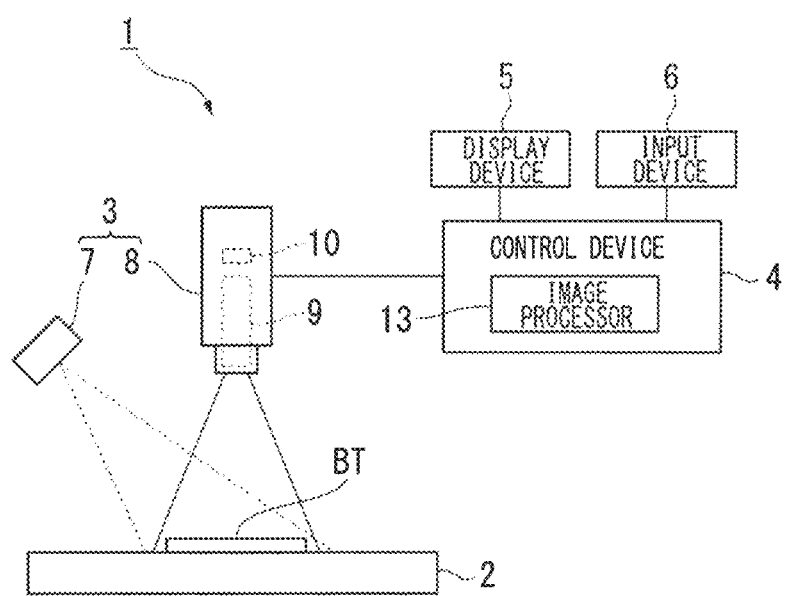
FIGS. 1A and 1B illustrate diagrams showing an imaging system, a detector, and an image generator according to an embodiment.
Figure 1B:
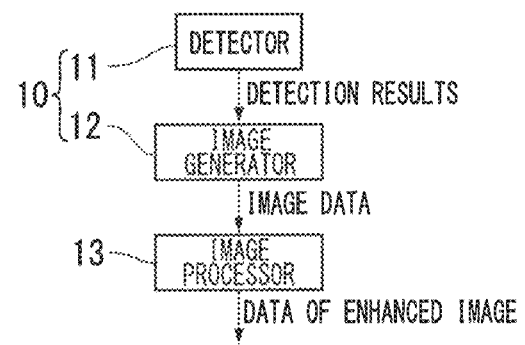

A first embodiment will be explained. FIG. 1A is a diagram showing an imaging system 1 according to the present embodiment. FIG. 1B is a diagram showing a detector 11 and an image generator 12 according to the present embodiment. The imaging system 1 is used for pathological diagnosis, for example. The imaging system 1 captures images of breast tissue BT while irradiating the tissue BT with infrared light having a predetermined wavelength. The tissue BT is surgically resected and may be fixed by using an organization fixative solution such as formalin (for example, formaldehyde solution). Furthermore, the tissue BT may be a part of a breast removed from a body by biopsy or the like, or breast tissue before removed from the breast (the tissue still belongs to the body).

Generally, the breasts consist of approximately 10% breast glands and approximately 90% adipose tissue (fatty area), which protects the breast glands. In breast cancer tissue (breast cancer area), the degree of approximation to water is higher than in the fatty area. For example, a portion in a breast that has a higher degree of approximation to water or has a lower degree of approximation to fat than a fatty area does possibly includes breast cancer tissue or breast cancer cell aggregation. The inventors of the present invention have found out that the wavelength bands from 950 nm or more to 1650 nm or less include a certain wavelength band that has a relatively large difference in light absorbance or a relatively large ratio of light absorbance between water and adipose tissue contained in the breasts.

Figure 2:
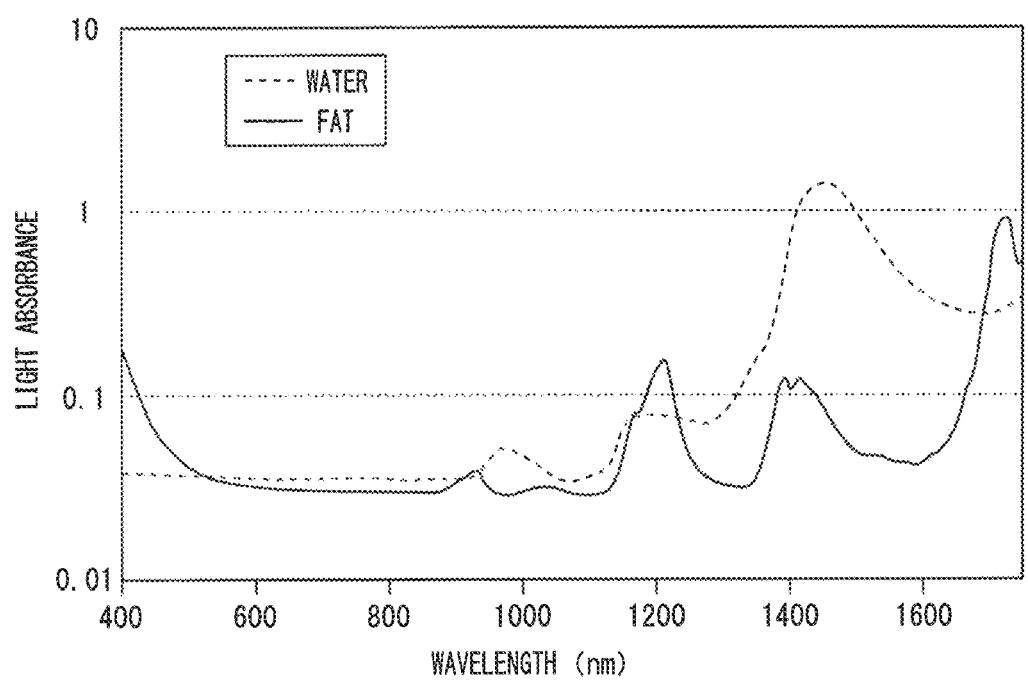
FIG. 2 is a graph showing measurement results of light absorbance of water and light absorbance of fat according to the present embodiment.

FIG. 2 is a graph showing measurement results of the light absorbance of water and the light absorbance of fat. In FIG. 2, the horizontal axis represents the wavelength and the vertical axis represents the light absorbance in logarithmic scale. "Water" samples have a thickness (optical path length of the cell) of 1 mm and "fat" samples have a thickness of 2 mm. FIG. 2 shows light absorbance in the wavelength bandwidth from 400 nm or more to 1750 nm or less. In FIG. 2, the light absorbance of water is represented by a dot line and the light absorbance of fat is represented by a solid line. As shown in FIG. 2, the wavelength bands from 950 nm or more to 1650 nm or less include a local maximum value or a local minimum value of the light absorbance of water and a local maximum value and a local minimum value of the light absorbance of fat. For example, the wavelength band from approximately 950 nm or more to approximately 990 nm or less includes a local maximum value of the light absorbance of water and a local minimum value of the light absorbance of fat. In the wavelength band from approximately 1050 nm or more to 1090 nm or less, the light absorbance of water increases from a local minimum value thereof, while the light absorbance of fat decreases toward a local minimum value thereof. In the wavelength band from approximately 1200 nm or more to 1350 nm or less, the light absorbance of water is substantially constant or increases, while the light absorbance of fat decreases toward a local minimum value thereof. In the wavelength band from approximately 1400 nm or more to approximately 1650 nm or less, the light absorbance of water is substantially maximum in the wavelength bandwidth in the graph, and the light absorbance of fat decreases from a local maximum value to a local minimum value thereof. For example, in the wavelength band from approximately 1400 nm or more to approximately 1450 nm or less, the light absorbance of water is substantially maximum in the wavelength bandwidth in the graph. For example, in the wavelength band from approximately 1500 nm or more to approximately 1650 nm or less, the light absorbance of fat is locally minimum. For example, when a layer of water is covered with a layer of fat, the layer of water may be detected by using a wavelength in which the light absorbance of water is higher than the light absorbance of fat. As explained above, among the wavelength bands from 950 nm or more to 1650 nm or less, the wavelength bands from 950 nm or more to 990 nm or less, the wavelength bands from 1050 nm or more to 1090 nm or less, the wavelength bands from 1200 nm or more to 1350 nm or less, the wavelength bands from 1400 nm or more to 1650 nm or less (hereinafter, referred to as predetermined wavelength bands), for example, have a relatively large difference in light absorbance or a relatively large ratio of light absorbance between water and fat. Specifically, the wavelength band from 1400 nm or more to 1650 nm or less has an extremely large difference in light absorbance or an extremely large ratio of light absorbance because of the large light absorbance of water, and thus water is easily discerned from fat in this wavelength band. Our experiments have revealed that breast gland adipose tissue has similar spectral properties on light absorbance to the corresponding properties of fat indicated by the data.

The inventors of the present invention have thought of detecting infrared light by capturing images of, among light radiated from breast tissue BT irradiated with infrared light (hereinafter, the term "infrared light" also includes a concept of "near infrared light"), infrared light having a wavelength selected from the predetermined wavelength bands, whereby an image will be obtained to indicate a portion with a high possibility of including one or both of breast cancer tissue and breast cancer cell aggregation. Moreover, the inventors of the present invention have thought of capturing images of infrared light having a wavelength in the predetermined wavelength bands to obtain images of an area showing characteristic light-absorbing properties of water and fat, whereby macropathological images of a tumor such as breast cancer will be obtained. The thus-obtained images are able to be used as, for example, images to specify a breast cancer area (one or both of an area containing breast cancer cell aggregation and an area containing breast cancer tissue) or images for clinical diagnosis, pathological diagnosis, or the like to specify a breast cancer area (one or both of an area containing breast cancer cell aggregation and an area containing breast cancer tissue). The imaging system 1 visualizes differences in light-absorbing properties between water and fat contained in breast tissue BT in images, for example, to contribute to improvement of accuracy in pathological diagnosis. As used herein, an area that includes one or both of an area containing breast cancer cell aggregation and an area containing breast cancer tissue is referred to as a breast cancer area, where the context permits.

Referring back to the description with reference to FIG. 1A, the imaging system 1 includes a stage device 2, an imaging apparatus 3, a control device 4, a display device (display, for example) 5, and an input device 6. The stage device 2 is able to have tissue BT disposed on the top surface thereof. The stage device 2 may include no mechanism to move breast tissue BT, such as a desk or a plate, or may have a mechanism to move breast tissue BT, such as an XY stage, for example. The imaging system 1 may include no stage device 2.

The imaging apparatus 3 includes an irradiator 7 and an imager 8. The irradiator 7 emits infrared light in wavelength bands including at least a part of the predetermined wavelength bands. The irradiator 7 includes an infrared light emitting diode (infrared LED), for example. The infrared LED emits infrared light that has a spectral half width of 100 nm or less, for example. The irradiator 7 emits infrared light having a peak wavelength (center wavelength) in the wavelength band from 1400 nm or more to 1650 nm or less, for example. The irradiator 7 emits infrared light in a narrow wavelength band (for example, with a half width of 100 nm or less) selected from the predetermined wavelength bands. As an example, the irradiator 7 is able to emit infrared light in a narrow wavelength band of 1400 nm, 1500 nm, or 1600 nm. For example, the imaging apparatus 3 includes an irradiator that irradiates breast tissue BT with infrared light with a peak wavelength in a single narrow wavelength band (for example, light having a single wavelength of 1400 nm, 1500 nm, 1600 nm, or the like) selected from the wavelength bands from 950 nm or more to 1650 nm or less or the wavelength bands from 1400 nm or more to 1650 nm or less, a detector that detects the infrared light among light radiated from the breast tissue BT irradiated with the infrared light, and an image generator that generates, on the basis of detection results from the detector, an image to specify a breast cancer area (one or both of an area containing breast cancer cell aggregation and an area in which breast cancer tissue) in the breast tissue BT.

Moreover, for example, the imaging apparatus 3 includes an irradiator that irradiates breast tissue BT with infrared light in a wavelength band with a peak wavelength of 1400 nm, a detector that detects light in a wavelength band with a peak wavelength of 1400 nm selected from the wavelength bands from 1400 nm or more to 1650 nm or less, among light radiated from the breast tissue BT irradiated with the infrared light, and an image generator that generates, on the basis of detection results from the detector, an image to specify a breast cancer area (one or both of an area containing breast cancer cell aggregation or an area containing breast cancer tissue) in the breast tissue BT.

The irradiator 7 may include a lamp light source such as a halogen lamp and a solid-state light source such as a laser diode. The irradiator 7 may be able to switch whether to emit infrared light or visible light. The irradiator 7 may emit light in a wavelength band other than the predetermined wavelength bands or light in a wide wavelength band including light in a wavelength band other than the narrow wavelength band, from a light source; and in this case, a filter may be used to select the wavelength band of light radiated to the breast tissue BT.

The imager 8 captures images of and thus detects light in a narrow wavelength band selected from the predetermined wavelength bands, among light radiated from the breast tissue BT irradiated with the infrared light. Light in a narrow wavelength band is, for example, light with a peak wavelength of 1400 nm, 1500 nm, or 1600 nm. The spectral half width of light in a narrow wavelength band is, for example, 100 nm or less. For example, when the irradiator 7 irradiates the breast tissue BT with infrared light in a narrow wavelength band, the imager 8 captures images of the breast tissue BT of a breast with which the infrared light is irradiated. Moreover, when the breast tissue BT is irradiated with light including light in a wavelength band other than the predetermined wavelength bands, the imager 3 may selectively detect light in the predetermined wavelength bands via, for example, a filter or the like to interrupt light that is not in the predetermined wavelength bands.

The imager 8 includes an imaging optical system 9 and an imaging element 10. The imaging optical system 9 includes a plurality of lens members to form an image of the breast tissue BT. The imaging element 10 includes a two-dimensional image sensor, such as a CMOS sensor or a CCD sensor, for example, to capture the image formed by the imaging optical system 9. The imaging element 10 has a plurality of pixels, for example, and has a structure in which a detector 11 (shown in FIG. 1B) such as a photodiode (photoelectric converting element) is disposed in each of the pixels. As an example, the photodiode applies indium gallium arsenide (InGaAs) or the like, thereby being able to detect light in the predetermined wavelength bands.

The imaging apparatus 3 includes a detector 11 and an image generator 12 as shown in FIG. 1B. The detector 11 and the image generator 12 are provided in the imaging element 10, for example. The detector 11 detects light radiated from the breast tissue BT, for example, by converting the light into an electric charge, and outputs the electric charge as a detection result. The image generator 12 generates, on the basis of the detection results from the detector 11, an image to specify a breast cancer area in the breast tissue BT (an image to specify a breast cancer portion in the breast tissue BT, an image by which a breast cancer portion in the breast tissue BT is able to be specified, an image to recognize a breast cancer portion in the breast tissue BT, an image by which a breast cancer portion in the breast tissue BT is able to be recognized, an image to determine a breast cancer portion in the breast tissue BT, an image based on which a breast cancer portion in the breast tissue BT is able to be determined, an image to discern a breast cancer portion in the breast tissue BT, an image based on which a breast cancer portion in the breast tissue BT is able to be discerned, or the like). The image to specify a breast cancer area is an image, for example, captured by irradiating the breast tissue BT with infrared light in a narrow wavelength band. The image generator 12 includes, for example, a readout circuit that reads out an electric charge from the detector 11. The image generator 12 may include an amplifier that amplifies the electric charge from the detector 11 and an analog-digital (AD) converter that converts the electric charge from the detector 11 to digital data. The image generator 12 outputs data of the image generated thereby to an image processor 13.

In the present embodiment, the imaging system 1 includes the image processor 13. The image processor 13 is provided in the control device 4, for example. The image processor 13 processes the image generated by the image generator 12 as shown in FIG. 1B. The image processor 13 adjusts the contrast of the image generated by the image generator 12 to make the image clearer, so as to generate an enhanced image in which the breast cancer area is enhanced, for example. The image processor 13 generates the enhanced image on the basis of the data of the image generated by the image generator 12, and outputs the enhanced image to the display device 5, for example.

The image generator 12 may generate, as an image to specify a breast cancer area, an image in which the contrast is adjusted (for example, an enhanced image). In this case, the image processor 13 may be a part of the image generator 12 and is provided in the imaging apparatus 3. The image processor 13 may be embedded in a device other than the control device 4, that is, may be embedded in the imager 8, for example. The imaging system 1 may include no image processor 13.

The imaging apparatus 3 may include an imager that is able to acquire visible light images in addition to infrared light images. The imaging system 1 may include an imaging apparatus that acquires visible light images in addition to the imaging apparatus 3. The imaging apparatus 3 may irradiate breast tissue BT with infrared light in a narrow wavelength band selected on the basis of the optical properties of water and the optical properties of fat to capture images of the tissue, so as to generate, on the basis of the captured result, an image to specify a breast cancer area in the tissue, for example.

Figure 3:
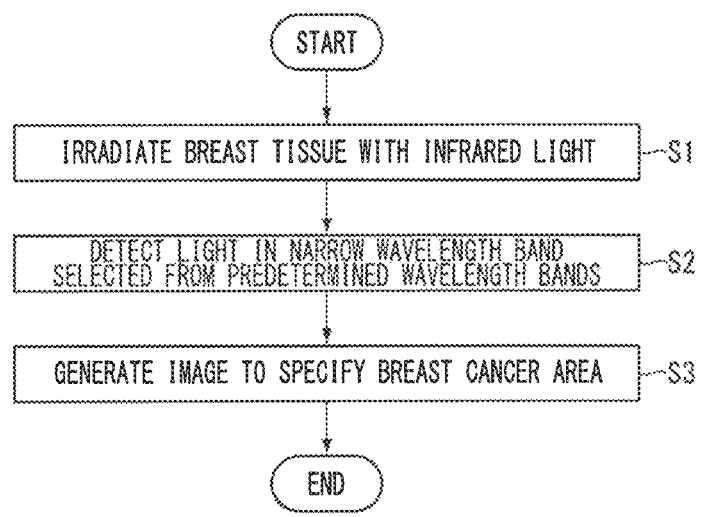
FIG. 3 is a flowchart showing an imaging method according to an embodiment.

Next, based on operations of the imaging system 1, an imaging method according to an embodiment is described. FIG. 3 is a flowchart showing an imaging method according to the present embodiment. At step S1, the imaging system 1 irradiates breast tissue BT with infrared light. This infrared light radiated is light in a narrow wavelength band (for example, 1400 nm, 1500 nm, 1600 nm, or the like) selected from the wavelength bands from 1400 nm or more to 1650 nm or less, for example. This infrared light has a peak wavelength in the above predetermined wavelength bands and has a spectral half width of 100 nm or less. As described above, the predetermined wavelength bands are selected on the basis of the optical properties of water and the optical properties of fat (for example, light absorbance and reflectance), for example.

At step S2, the imaging apparatus 3 detects light in a narrow wavelength band among the predetermined wavelength bands. For example, when the breast tissue BT is irradiated with infrared light in a narrow wavelength band at step S1, the imaging apparatus 3 captures images of the breast tissue BT irradiated with the infrared light at step S2. At step S3, the imaging apparatus 3 generates an image to specify a breast cancer area on the basis of the infrared light detected at step S2. For example, the image generator 12 generates an image on the basis of the detection results from the detector 11. At step S3, the imaging processor 13 may generate an enhanced image with an enhanced portion that has a high possibility of being breast cancer tissue or breast cancer cell aggregation, for example, as an image to specify a breast cancer area. The imaging system 1 displays an image to specify a breast cancer area, for example, on the display device 5. The imaging method to obtain information on breast cancer tissue or breast cancer cell aggregation may be a method that includes irradiating breast tissue with infrared light in a narrow wavelength band selected on the basis of the optical properties of water and the optical properties of fat to capture images of the tissue, and generating, on the basis of the capturing result, an image to specify a breast cancer area in the tissue.

Figure 4A:
FIGS. 4A and 4B illustrate images showing a sample according to Example 1 and pathological diagnostic results.
Figure 4B:
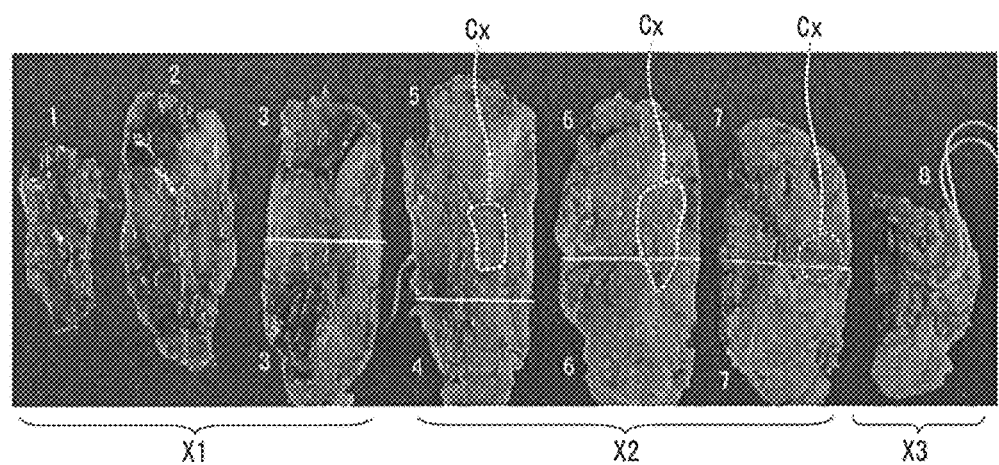

Next, using FIGS. 4A, 4B, 5A to 5F, 6A, 6B, and 7A to 7F, an example of images (infrared images) obtained by capturing, by the imaging system 1, images of a sample (breast tissue BT) taken by surgically resecting a part of a breast of a human subject is explained. FIG. 4A is an image showing a sample according to Example 1 (visible image obtained by capturing an image of a sample by visible light), and FIG. 4B is an image showing pathological diagnostic results of the sample. FIGS. 4A and 4B are images of the sample obtained by converting color images of the sample captured by a visible light camera into gray scale images. The sample in FIG. 4A is shown in such a manner that a piece of breast tissue surgically resected is fixed in formalin, sliced into sections of approximately 5 mm thick, and the sliced sections are lined side by side in the order in which they are in the tissue from the deepest. As shown in FIG. 4B, the pathological diagnosis resulted in no breast cancer tissue in three sections X1, breast cancer tissue Cx found in three sections X2, and no breast cancer tissue in one section X3.

Figure 5A:
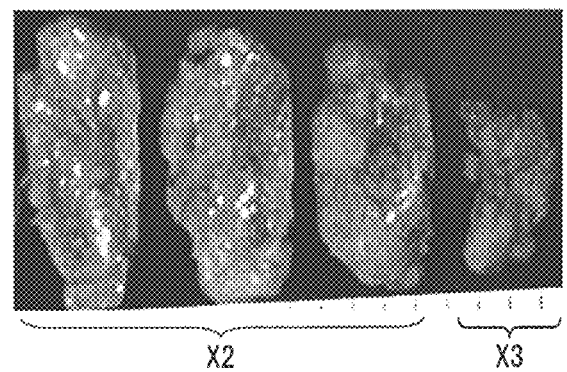
FIGS. 5A to 5F illustrate images captured by the imaging system in Example 1.
Figure 5B:
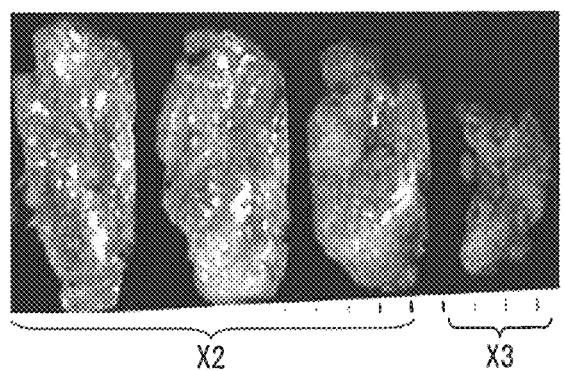
Figure 5C:
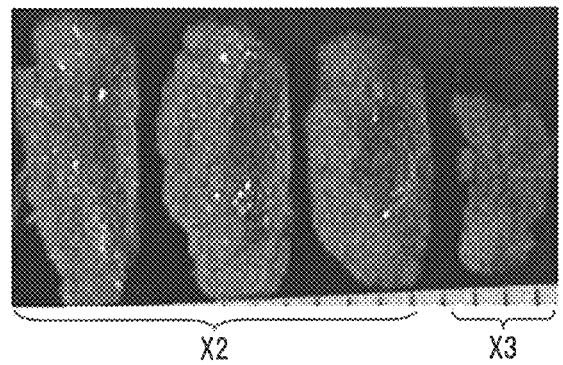
Figure 5D:
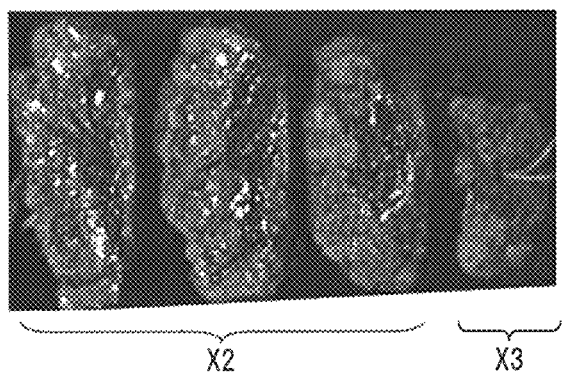
Figure 5E:
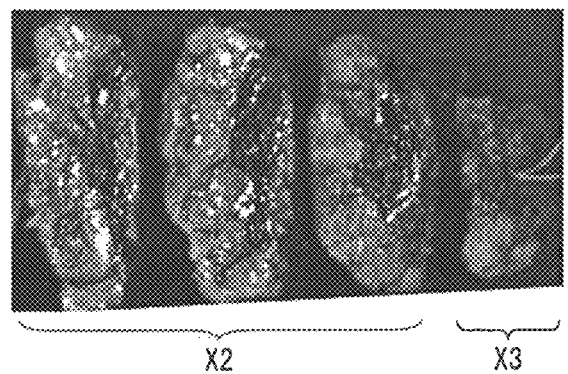
Figure 5F:
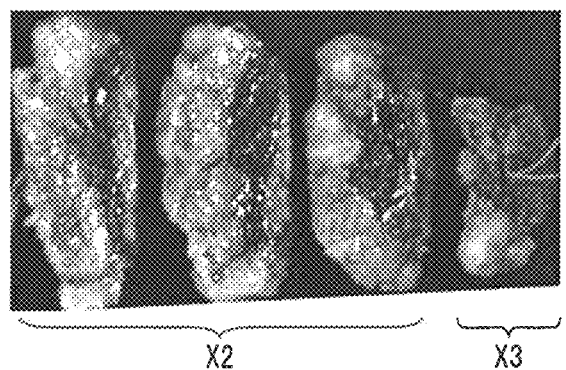

FIGS. 5A to 5F are drawings showing images (infrared images) of the sample captured by the imaging system 1 in Example 1. FIGS. 5A to 5F are parts of the sections X2 (sections each including the breast cancer tissue Cx) and a part of the section X3 (section including no breast cancer tissue Cx) in FIG. 4B. FIG. 5A corresponds to results of detecting infrared light having a center wavelength of 970 nm, via a sample (breast tissue BT), after irradiation of the sample with the infrared light. Similarly, FIGS. 5B to 5F correspond to results of detecting infrared light having center wavelengths of 1070 nm, 1300 nm, 1400 nm, 1500 nm, and 1600 nm, respectively. In respective wavelengths bands employed in FIGS. 5A to 5F, the light absorbance of water is higher than the light absorbance of fat, and the portion of the sample corresponding to water absorbs a larger amount of infrared light than the portion corresponding to fat does, so that the portion corresponding to water looks darker than the portion corresponding to fat. In particular, FIGS. 5D to 5F show portions where extremely large amounts of water are absorbed, thus it is easy to discern the portion corresponding to water from the portion corresponding to fat. Such a darker portion corresponds reasonably well with a portion pathologically diagnosed as having the breast cancer tissue Cx in FIG. 4B, and it is ensured that the present embodiment enables reliable information on the breast cancer tissue to be obtained from captured images (infrared images).

Figure 6A:
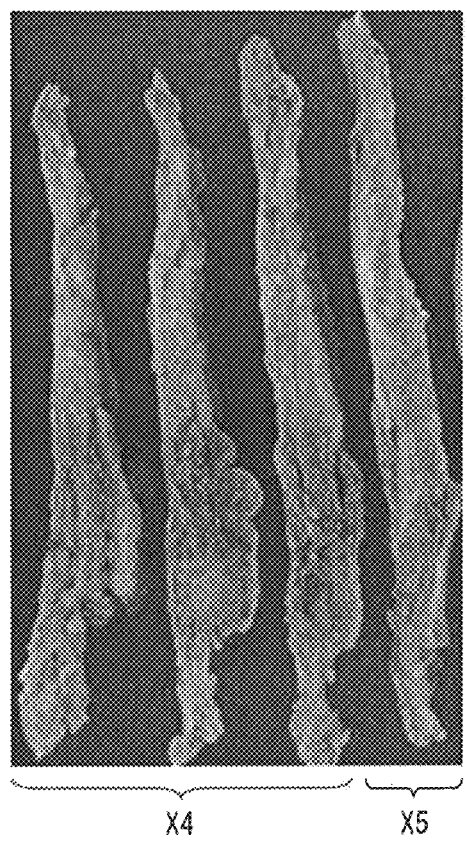
FIGS. 6A and 6B illustrate images showing a sample according to Example 2 and pathological diagnostic results.
Figure 6B:
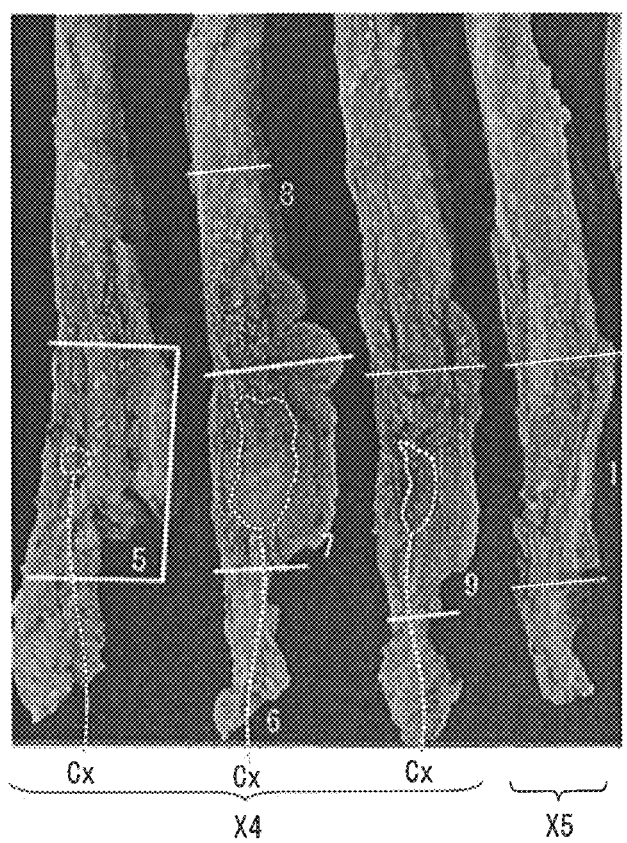

FIG. 6A is an image (visible image) showing a sample according to Example 2 and FIG. 6B is an image showing pathological diagnostic results of the sample. FIGS. 6A and 6B are images of the sample obtained by converting color images of the sample captured by a visible light camera into gray scale images. The sample in FIG. 6A is shown in such a manner that a piece of breast tissue surgically resected is sliced into sections of approximately 5 mm thick, and the sliced sections are lined side by side in the order in which they are in the tissue from the deepest. As shown in FIG. 6B, the pathological diagnosis resulted in breast cancer tissue Cx found in three sections X4 and no breast cancer tissue in one section X5.

Figure 7A:
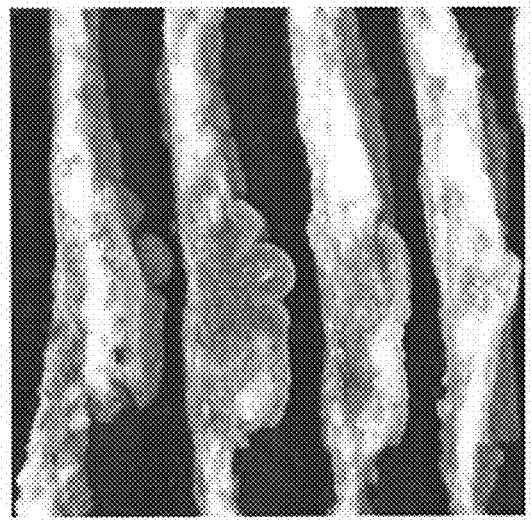
FIGS. 7A to 7F illustrate images captured by the imaging system in Example 2.
Figure 7B:
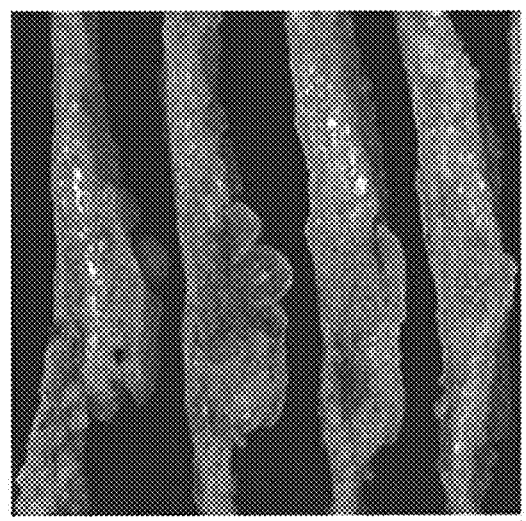
Figure 7C:
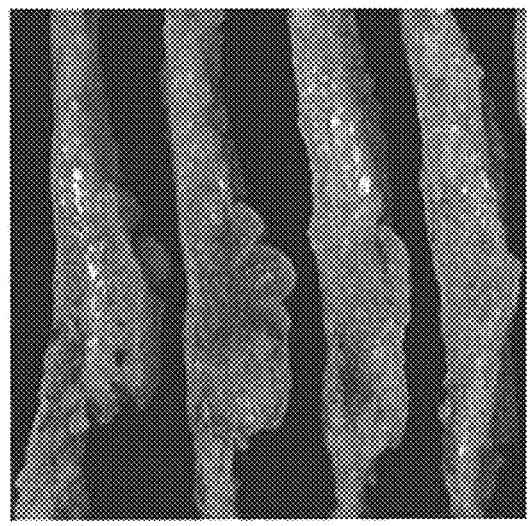
Figure 7D:
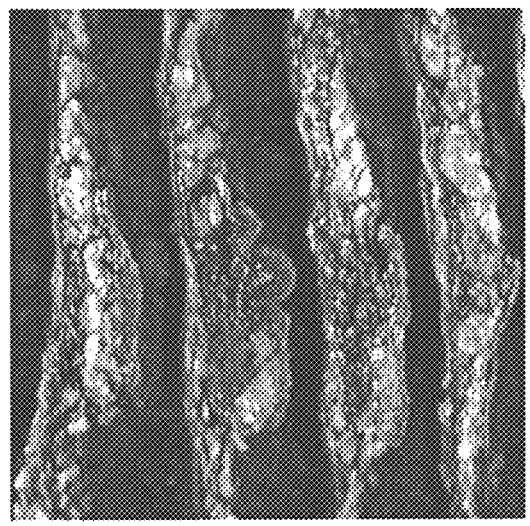
Figure 7E:
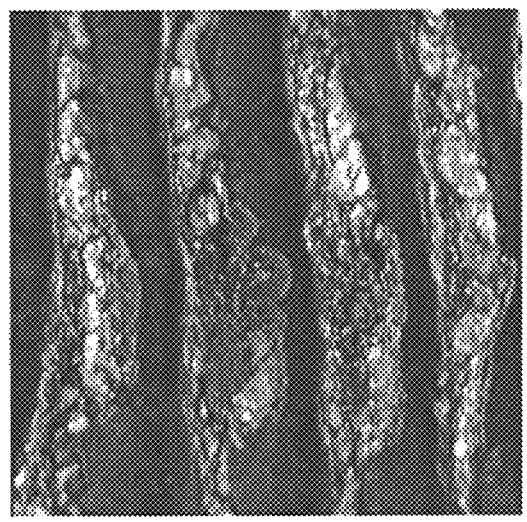
Figure 7F:
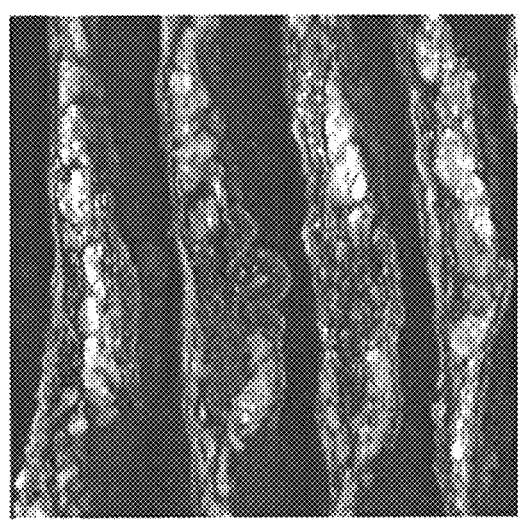

FIGS. 7A to 7F are drawings showing images (infrared images) of the sample captured by the imaging system 1 in Example 2. FIGS. 7A to 7F correspond to results of detecting infrared light having center wavelengths of 970 nm, 1070 nm, 1300 nm, 1400 nm, 1500 nm, and 1600 nm, respectively. In FIGS. 7A to 7F, the portion corresponding to water absorbs a larger amount of infrared light than the portion corresponding to fat does, so that the portion corresponding to water looks darker than the portion corresponding to fat. In particular, FIGS. 7D to 7F show portions where extremely large amounts of water are absorbed, thus it is easy to discern the portion corresponding to water from the portion corresponding to fat. Such a darker portion corresponds reasonably well with a portion pathologically diagnosed as having the breast cancer tissue Cx in FIG. 6B, and it is ensured that the present embodiment enables reliable information on the breast cancer tissue to be obtained from captured images (infrared images).

Figure 8A:
FIGS. 8A to 8F illustrate an image showing a sample according to Example 3, infrared images, and an image showing a comparison between an estimated area of breast cancer tissue obtained from the infrared images and pathological diagnostic results.
Figure 8B:
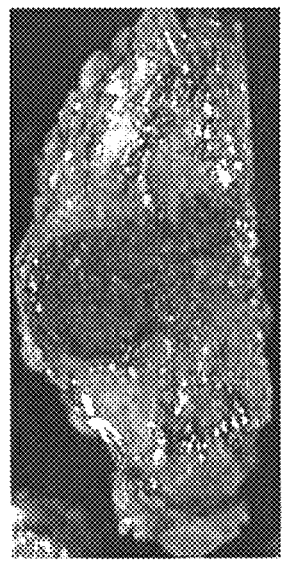
Figure 8C:
Figure 8D:
Figure 8E:
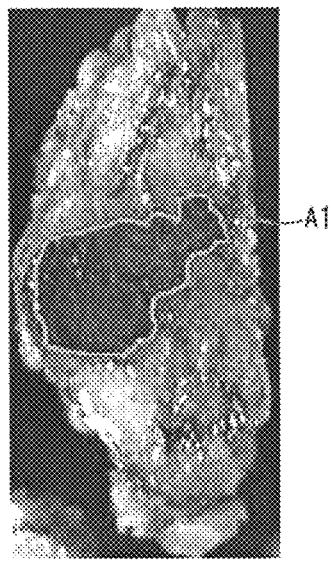
Figure 8F:
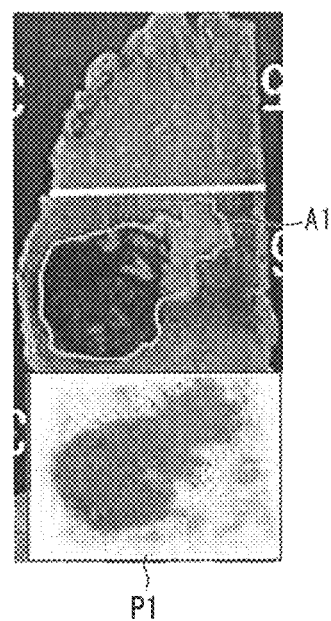

FIG. 8A is an image (visible image) showing a sample according to Example 3. FIG. 8A is an image of the sample obtained by converting a color image of the sample captured by the visible light camera into a gray scale image. This sample includes nodular lesions with adipose tissue as a background, and pathological diagnostic results indicate an invasive ductal carcinoma (invasive Ca) found therein. FIGS. 8B to 8D are infrared images obtained by irradiating the sample with infrared light having wavelengths of 1400 nm, 1500 nm, and 1600 nm, respectively. FIG. 8E is an image showing an area of breast cancer estimated by a doctor through visual inspections on the basis of the image in FIG. 8D (hereinafter referred to as an estimated area A1). FIG. 8F is an image in which the visible image in FIG. 8A is overlapped with the estimated area A1 of the breast cancer in FIG. 8E to show a comparison between the estimated area A1 and a pathological diagnostic result P1. As shown in FIG. 8F, the estimated area A1 of the breast cancer obtained by the doctor through the visual inspections corresponds reasonably well with the pathological diagnostic result, and it is ensured that reliable information on the breast cancer tissue is able to be acquired.

Figure 9A:
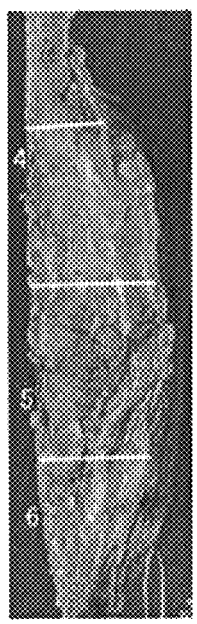
FIGS. 9A to 9F illustrate an image showing a sample according to Example 4, infrared images, and an image showing a comparison between an estimated area of breast cancer tissue obtained from the infrared images and pathological diagnostic results.
Figure 9B:
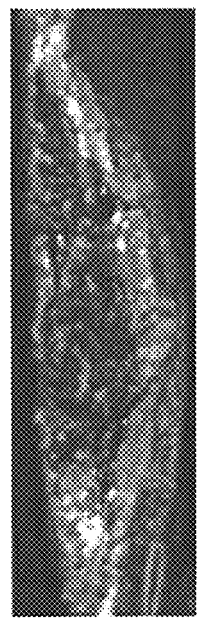
Figure 9C:
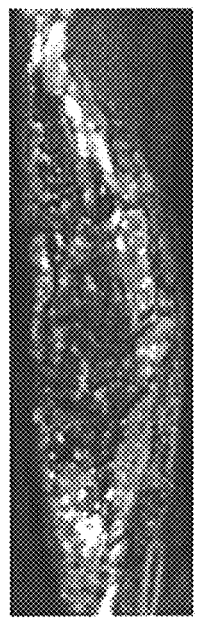
Figure 9D:
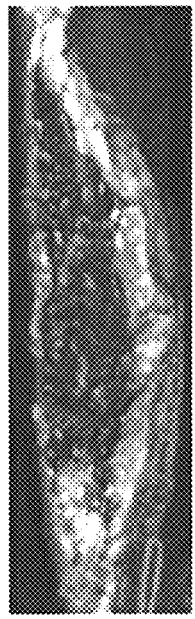
Figure 9E:
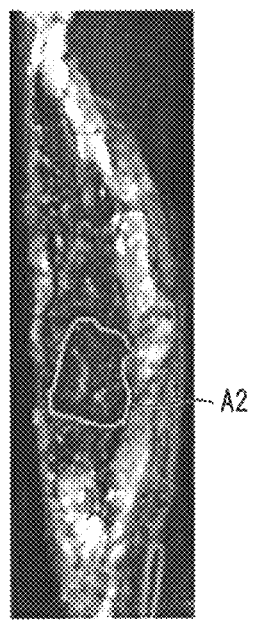
Figure 9F:
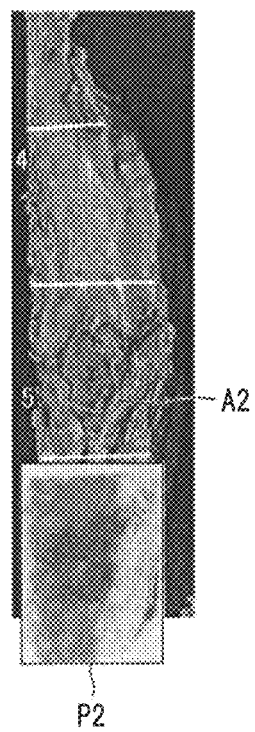

FIG. 9A is an image (visible image) showing a sample according to Example 4. FIG. 9A is an image of the sample obtained by converting a color image of the sample captured by the visible light camera into a gray scale image. This sample includes nodular lesions with fibrous connective tissue as a background, and pathological diagnostic results indicate an invasive ductal carcinoma (invasive Ca) found therein. FIGS. 9B to 9D are infrared images obtained by irradiating the sample with infrared light having wavelengths of 1400 nm, 1500 nm, and 1600 nm, respectively. FIG. 9E is an image showing an area of breast cancer estimated by a doctor through visual inspections on the basis of the image in FIG. 9D (hereinafter referred to as an estimated area A2). FIG. 9F is an image in which the visible image in FIG. 9A is overlapped with the estimated area A2 of the breast cancer in FIG. 9E to show a comparison between the estimated area A2 and a pathological diagnostic result P2. As shown in FIG. 9F, the estimated area A2 of the breast cancer obtained by the doctor through the visual inspections corresponds reasonably well with the pathological diagnostic result, and it is ensured that reliable information on the breast cancer tissue is able to be acquired.

Figure 10A:
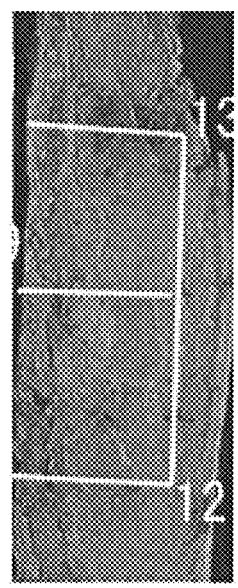
FIGS. 10A to 10F illustrate an image showing a sample according to Example 5, infrared images, and an image showing a comparison between an estimated area of breast cancer tissue obtained from the infrared images and pathological diagnostic results.
Figure 10B:
Figure 10C:
Figure 10D:
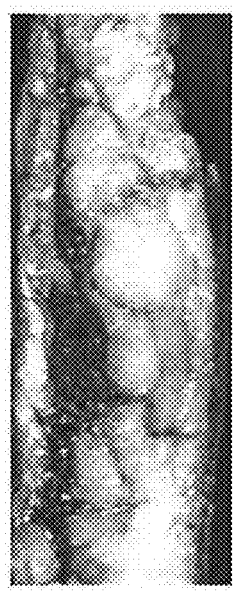
Figure 10E:
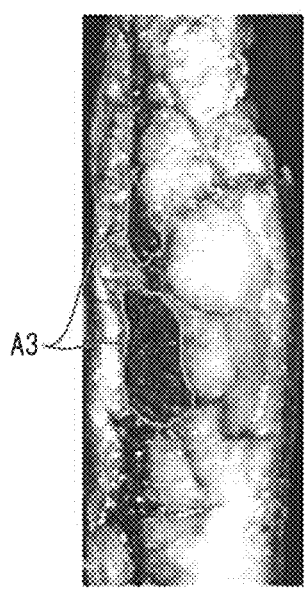
Figure 10F:
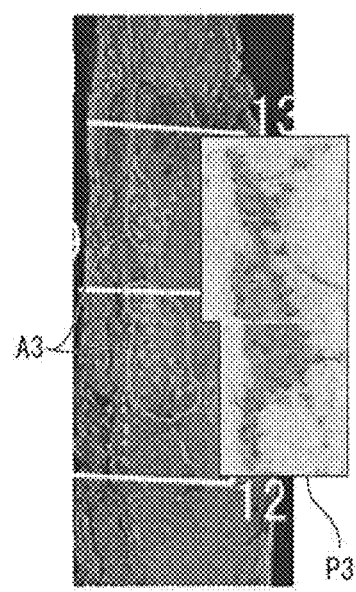

FIG. 10A is an image (visible image) showing a sample according to Example 5. FIG. 10A is an image of the sample obtained by converting a color image of the sample captured by the visible light camera into a gray scale image. This sample includes non-nodular lesions, and pathological diagnostic results indicate a ductal carcinoma in situ (DCIS) found therein. FIGS. 10B to 10D are infrared images obtained by irradiating the sample with infrared light having wavelengths of 1400 nm, 1500 nm, and 1600 nm, respectively. FIG. 10E is an image showing an area of breast cancer estimated by a doctor through visual inspections on the basis of the image in FIG. 10D (hereinafter referred to as an estimated area A3). FIG. 10F is an image in which the visible image in FIG. 10A is overlapped with the estimated area A3 of the breast cancer in FIG. 10E to show a comparison between the estimated area A3 and a pathological diagnostic result P3. As shown in FIG. 10F, the estimated area A3 of the breast cancer obtained by the doctor through the visual inspections corresponds reasonably well with the pathological diagnostic result, and it is ensured that reliable information on the breast cancer tissue is able to be acquired.

Comparison between the estimated areas described with reference to FIGS. 8A to 8F, 9A to 9F, 10A to 10F and the pathological diagnostic results was performed for 108 cases. The comparison results indicate that, for 95% (19/20 cases) of the sections including only nodular lesions with adipose tissue as a background, the estimated areas correspond reasonably well with the respective pathological diagnostic results. For approximately 53% (8/15 cases) of the sections including only nodular lesions with fibrous connective tissue as a background, the estimated areas correspond reasonably well with the pathological respective diagnostic results. For approximately 16% (4/25 cases) of the sections including only non-nodular lesions, the estimated areas correspond reasonably well with the respective pathological diagnostic results. For approximately 74% (23/31 cases) of the sections each including both nodular lesions with adipose tissue as a background and non-nodular lesions, the estimated areas correspond reasonably well with the respective pathological diagnostic results. For approximately 29% (5/17 cases) of the sections each including both nodular lesions with fibrous connective tissue as a background and non-nodular lesions, the estimated areas correspond reasonably well with the respective pathological diagnostic results. As described above, the imaging apparatus 3 of each of the examples is able to generate an image to specify a breast cancer area using an estimated area in infrared images obtained by radiating the infrared light.

In the present embodiment, the control device 4 includes a computer system, for example. The control device 4 loads a control program stored in a memory device (not shown) such as a hard disk to execute various kinds of processing in accordance with the control program. This control program causes a computer, for example, to control processing including: irradiating breast tissue with infrared light, detecting infrared light in a narrow wavelength band selected from wavelength bands from 1400 nm or more to 1650 nm or less, among light radiated from the tissue irradiated with the infrared light, and generating, on the basis of the detected light in the narrow wavelength band, an image to specify a breast cancer area in the tissue. This program may be provided by being recorded in a computer-readable recording medium (for example, optical disc or magnetic disk).

[Surgery Support System]

Figure 11:
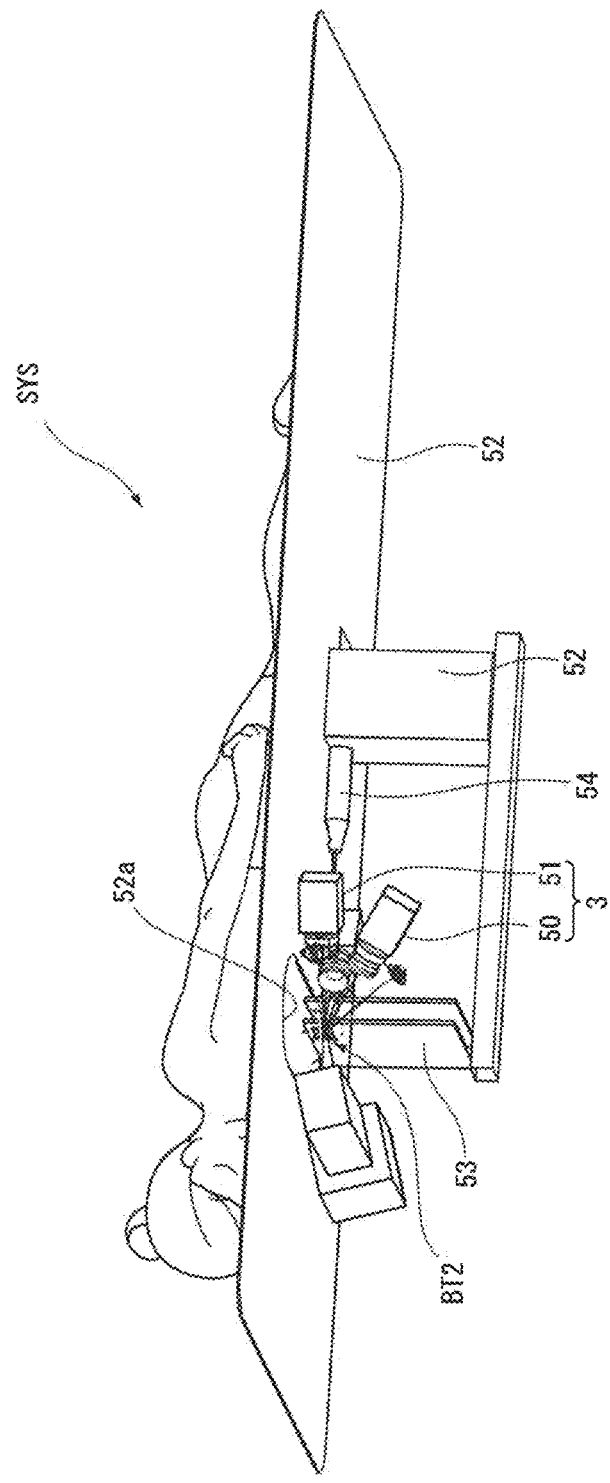
FIG. 11 is a diagram showing an example of a surgery support system according to an embodiment.

In the above embodiment, an example of using the imaging apparatus 3 for pathological diagnosis is described, whereas the imaging apparatus 3 is also able to be used for a surgery support system (medical support system). FIG. 11 is a diagram showing an example of a surgery support system SYS. This surgery support system SYS is a mammography apparatus using the imaging apparatus 3 (imaging system 1) described in the above embodiment.

The surgery support system SYS includes a bed 52, a transparent plastic plates 53, and a perforation needle 54. The bed 52 is a bed on which an examinee lies facing down. The bed 52 has an aperture 52a through which a breast BT2 (tissue) of the examinee as a subject is exposed downward. The transparent plastic plates 53 are used to sandwich the breast BT2 from both side thereof to flatten the breast BT2. The perforation needle 54 is an operation device that is able to treat the tissue. The perforation needle 54 is inserted into the breast BT2 in a core needle biopsy to take a sample.

The imaging apparatus 3 includes an illumination unit 50 (irradiator) and an infrared camera 51 (imager). The illumination unit 50 irradiates breast tissue BT2 with infrared light. The infrared camera 51 detects infrared light radiated from the tissue. With the breast BT2 pressed by the transparent plastic plates 53 from both sides to be flattened, the illumination unit 50 irradiates the breast BT2 with infrared light in predetermined wavelength bands, and the infrared camera 51 obtains an image of the breast BT2 with reflected infrared light from the illumination unit 50.

The surgery support system SYS is, for example, able to capture images of a breast cancer area (for example, breast cancer tissue) in the breast BT2 with the imaging apparatus 3 and insert the perforation needle 54 to the breast BT2 so as to sample the tissue while displaying (or outputting) the images on the display device 5 (for example, display) or projecting the images onto the tissue (for example, breast BT2) of the subject. The surgery support system SYS is able to obtain reliable information on breast cancer tissue in a breast with the use of the imaging apparatus 3. An operator is, for example, able to insert the perforation needle 54 to a portion having a high possibility of including breast cancer tissue in the breast BT2 while observing images generated by an image analyzer.

The technical scope of the present invention is not limited to the above-described embodiments or the like. One or more elements described in the above-described embodiments or the like may be omitted. The elements described in the above-described embodiments or the like are able to be combined as appropriate. Insofar as is permitted by law, the disclosures of all documents cited in the above-described embodiments or the like are incorporated herein.

What is claimed is:

1. An imaging method comprising:
   irradiating breast tissue with infrared light;
   detecting light in a narrow wavelength band selected from wavelength bands from 1400 nm or more to 1650 nm or less, among light radiated from the tissue irradiated with the infrared light; and
   generating, based on the detected light in the narrow wavelength band, an image to specify an area in the tissue containing breast cancer cell aggregation or breast cancer tissue,
   wherein a peak wavelength of the infrared light is set to 1400 nm or more to 1650 nm or less,
   wherein the infrared light has a spectral half width of 100 nm or less.

2. The imaging method of claim 1, wherein the narrow wavelength band is selected based on optical properties of water and optical properties of fat.

3. The imaging method of claim 1, wherein the light in the narrow wavelength band is light having a wavelength of 1400 nm, 1500 nm, or 1600 nm.

4. The imaging method of claim 1, wherein the breast cancer cell aggregation or the breast cancer tissue includes an invasive ductal carcinoma.

5. The imaging method of claim 1, wherein the breast cancer cell aggregation or the breast cancer tissue includes a ductal carcinoma in situ.

6. The imaging method of claim 1, wherein the tissue includes a non-nodular lesion.

7. The imaging method of claim 1, wherein the tissue includes a nodular lesion with adipose tissue as a background.

8. An imaging apparatus comprising:
   an irradiator that irradiates breast tissue with infrared light;
   a detector that detects light in a narrow wavelength band selected from wavelength bands from 1400 nm or more to 1650 nm or less, among light radiated from the tissue irradiated with the infrared light; and
   an image generator that generates, based on detection results from the detector, an image to specify an area in the tissue containing breast cancer cell aggregation or breast cancer tissue,
   wherein a peak wavelength of the infrared light is set to 1400 nm or more to 1650 nm or less,
   wherein the infrared light has a spectral half width of 100 nm or less.

9. The imaging apparatus of claim 8, wherein the narrow wavelength band is selected based on optical properties of water and optical properties of fat.

10. The imaging apparatus of claim 8, wherein the light in the narrow wavelength band is light having a wavelength of 1400 nm, 1500 nm, or 1600 nm.

11. The imaging apparatus of claim 8, wherein the irradiator includes a light emitting diode or a laser diode.

12. The imaging apparatus of claim 8, wherein the breast cancer cell aggregation or the breast cancer tissue includes an invasive ductal carcinoma.

13. The imaging apparatus of claim 8, wherein the breast cancer cell aggregation or the breast cancer tissue includes a ductal carcinoma in situ.

14. The imaging apparatus of claim 8, wherein the tissue includes a non-nodular lesion.

15. The imaging apparatus of claim 8, wherein the tissue includes a nodular lesion with adipose tissue as a background.

16. An imaging system comprising:
    the imaging apparatus of claim 8; and
    a display device that displays images of the tissue captured by the imaging apparatus.

17. The imaging system of claim 16 comprising: a second imaging apparatus that detects a visible light image of the tissue.

18. A surgery support system comprising:
    the imaging apparatus of claim 8; and
    an operation device that is capable of processing the tissue.

19. An imaging apparatus comprising:
    an irradiator that irradiates tissue with infrared light;
    a detector that detects first light in a wavelength band selected from predetermined wavelength bands from 1050 nm or more to 1650 nm or less, among light radiated from the tissue irradiated with the light; and
    an image generator that generates, based on detection results from the detector, an image to specify a breast cancer area in the tissue,
    wherein the infrared light has a spectral half width of 100 nm or less.

20. The imaging apparatus of claim 19, wherein the selected wavelength band is selected based on optical properties of water or optical properties of fat.

21. The imaging apparatus of claim 6, wherein
    the detector detects second light in a wavelength band, the wavelength band being selected from the predetermined wavelength bands from 1050 nm or more to 1650 nm or less and being different from the wavelength band of the first light, and
    the image generator generates, based on detection results from the detector after detecting the second light, an image to specify a breast cancer area in the tissue.

22. The imaging apparatus of claim 19, wherein the first light has a wavelength selected from 1350 nm or more to 1650 nm or less.

23. The imaging apparatus of claim 19, wherein the first light is light having a wavelength of 1400 nm, 1500 nm, or 1600 nm.

24. The imaging apparatus of claim 19, wherein the first light is light having a wavelength of 1070 nm or 1300 nm.

25. The imaging apparatus of claim 19, wherein the image generator generates the image in which the breast cancer area is enhanced.

26. The imaging apparatus of claim 19, wherein the image generator generates the image in which contract is adjusted.

27. The imaging apparatus of claim 19, wherein the detector includes a filter that interrupts light other than light in a wavelength band selected from the predetermined wavelength bands.

28. The imaging apparatus of claim 19, wherein the breast cancer area includes an invasive ductal carcinoma.

29. The imaging apparatus of claim 19, wherein the breast cancer area includes a ductal carcinoma in situ.

30. The imaging apparatus of claim 19, wherein the tissue includes a non-nodular lesion.

31. The imaging apparatus of claim 19, wherein the tissue includes a nodular lesion with adipose tissue as a background.

32. An imaging system comprising:
the imaging apparatus of claim 19; and
a display device that displays images of the tissue captured by the imaging apparatus.

33. A storage medium storing therein a control program that causes a computer to control processing comprising:
irradiating breast tissue with infrared light;
detecting light in a narrow wavelength band selected from wavelength bands from 1400 nm or more to 1650 nm or less, among light radiated from the tissue irradiated with the infrared light; and
generating, based on the detected light in the narrow wavelength band, an image to specify an area in the tissue containing breast cancer cell aggregation or breast cancer tissue,
wherein a peak wavelength of the infrared light is set to 1400 nm or more to 1650 nm or less,
wherein the infrared light has a spectral half width of 100 nm or less.

34. A storage medium storing therein a control program that causes a computer to control processing comprising:
irradiating tissue with infrared light;
detecting first light in a narrow wavelength band selected from wavelength bands from 1050 nm or more to 1650 nm or less, among light radiated from the tissue irradiated with the infrared light; and
generating, based on the detected first light, an image to specify a breast cancer area in the tissue,
wherein the infrared light has a spectral half width of 100 nm or less.

* * * * *